United States Patent
Lim et al.

(10) Patent No.: US 8,480,739 B2
(45) Date of Patent: Jul. 9, 2013

(54) C1-C2 IMPLANT AND METHODS OF USE

(75) Inventors: Roy K. Lim, Germantown, TN (US); Peter Robertson, Auckland (NZ)

(73) Assignee: Warsaw Orthopedic, Inc., Warsaw, IN (US)

( * ) Notice: Subject to any disclaimer, the term of this patent is extended or adjusted under 35 U.S.C. 154(b) by 233 days.

(21) Appl. No.: 12/854,534

(22) Filed: Aug. 11, 2010

(65) Prior Publication Data

US 2012/0041558 A1 Feb. 16, 2012

(51) Int. Cl.
*A61F 2/44* (2006.01)

(52) U.S. Cl.
USPC ...................................... 623/17.11

(58) Field of Classification Search
USPC ........................... 623/17.11–17.16
See application file for complete search history.

(56) References Cited

U.S. PATENT DOCUMENTS

| | | | |
|---|---|---|---|
| 6,235,059 B1 * | 5/2001 | Benezech et al. | 623/17.16 |
| 7,591,851 B2 | 9/2009 | Winslow et al. | |
| 7,601,170 B2 | 10/2009 | Winslow et al. | |
| 2002/0026243 A1 | 2/2002 | Lin | |
| 2004/0193269 A1 * | 9/2004 | Fraser et al. | 623/17.11 |
| 2005/0273100 A1 | 12/2005 | Taylor | |
| 2005/0277929 A1 | 12/2005 | Raiszadeh | |
| 2006/0004363 A1 | 1/2006 | Brockmeyer et al. | |
| 2006/0235391 A1 | 10/2006 | Sutterlin | |
| 2007/0055373 A1 | 3/2007 | Hudgins et al. | |
| 2007/0123863 A1 | 5/2007 | Winslow et al. | |
| 2007/0123872 A1 | 5/2007 | Brockmeyer et al. | |
| 2008/0033557 A1 | 2/2008 | Pasquet et al. | |
| 2008/0051890 A1 * | 2/2008 | Waugh et al. | 623/17.11 |
| 2008/0161925 A1 | 7/2008 | Brittan et al. | |
| 2009/0177237 A1 | 7/2009 | Zucherman et al. | |
| 2009/0182377 A1 | 7/2009 | Petersen | |
| 2009/0210062 A1 | 8/2009 | Thalgott et al. | |

* cited by examiner

Primary Examiner — Sameh Boles (57) ABSTRACT

An implant for positioning between the C1 and C2 vertebral members. The implants may include a blade sized to be inserted between the C1 and C2 members. The blade may include a length measured between an insertion tip and a second side, and a height measured between a superior side that contacts against the C1 vertebral member and an inferior side that contacts against the C2 vertebral member. A leg may be positioned at the second side of the blade. The leg may extend outward below the inferior side of the blade and away from second side of the blade to extend across an exterior of the C2 vertebral member. An aperture is positioned to extend through the implant. The implant may extend through the blade or may extend through a flange that extends from the blade.

5 Claims, 11 Drawing Sheets

C1-C2 IMPLANT AND METHODS OF USE

BACKGROUND

The present application is directed to an implant for spacing apart vertebral members and, more particularly, to an implant configured to be positioned between the C1-C2 articular joint.

The spine is divided into four regions comprising the cervical, thoracic, lumbar, and sacrococcygeal regions. The cervical region includes the top seven vertebral members of the spine identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, flange, lateral bending, and rotation.

The cervical region is further divided into an upper cervical region that includes the C1 and C2 vertebral members, and the lower cervical region that includes the C3-C7 vertebral members. The C1 vertebral member includes a bony ring with wide lateral masses that extend to each side and have large, inferior surfaces that articulate with the C2 vertebral member. The C2 vertebral member includes lateral masses each with a superior articular facet that form a pair of articular joints with the C1 lateral masses. The C2 vertebral member acts as a pivot point for the C1 vertebral member with the primary range of movement between the vertebral members being rotational.

Atlantoaxial subluxation is the misalignment of the C1 and C2 vertebral members and may occur from a variety of conditions, such as major trauma, or a degenerative condition such as rheumatoid arthritis or osteoarthritis. Atlantoaxial subluxation may cause pain, headaches, or cervical spinal cord compression.

Fusion of the C1-C2 vertebral members is often prescribed to treat atlantoaxial subluxation. Fusion in this region of the spine is difficult because of the relative small working space requiring the fusion procedure to occur within the anatomic constraints of the patient. Previous fusion techniques have been difficult due to the placement of fasteners within one or both of the vertebral members. The difficulties may occur because of abnormalities in one or both vertebral members, or destruction of the articular joints due to bone loss at either vertebral member.

SUMMARY

The present application is directed to implants for positioning between the C1 and C2 vertebral members. The implants may include a blade sized to be inserted between the C1 and C2 members. The blade may include a length measured between an insertion tip and a second side, and a height measured between a superior side that contacts against the C1 vertebral member and an inferior side that contacts against the C2 vertebral member. A leg may be positioned at the second side of the blade. The leg may extend outward below the inferior side of the blade and away from second side of the blade to extend across an exterior of the C2 vertebral member. An aperture is positioned to extend through the implant. The implant may extend through the blade or may extend through a flange that extends from the blade.

The various aspects of the various embodiments may be used alone or in any combination, as is desired.

DETAILED DESCRIPTION

The present application is directed to an implant configured to be positioned within the articular joint formed between the C1-C2 vertebral members. The implant is shaped and sized for positioning between the C1 and C2 vertebral members, and to receive and position one or more fasteners at one or more placement points for attachment to the vertebral members.

Figure 1:
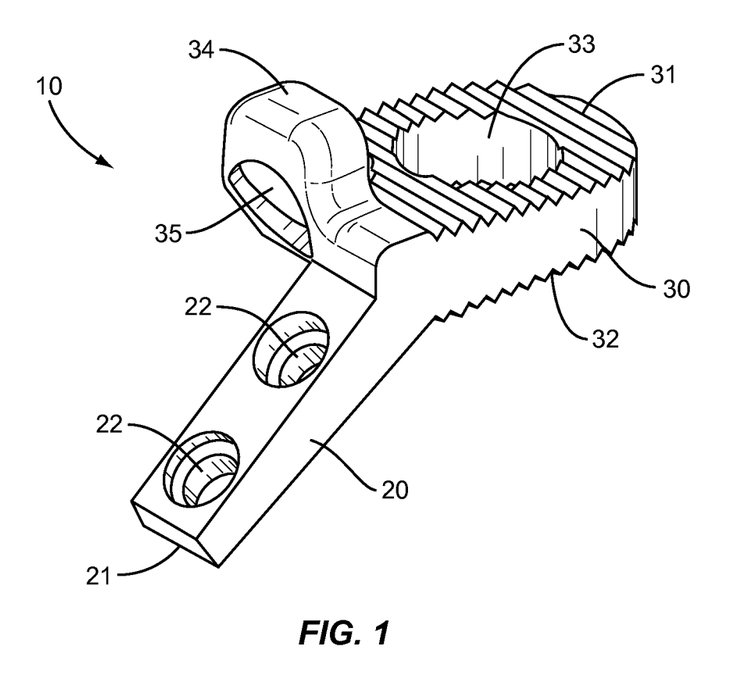
FIG. 1 is a perspective view of an implant according to one embodiment.
Figure 2:
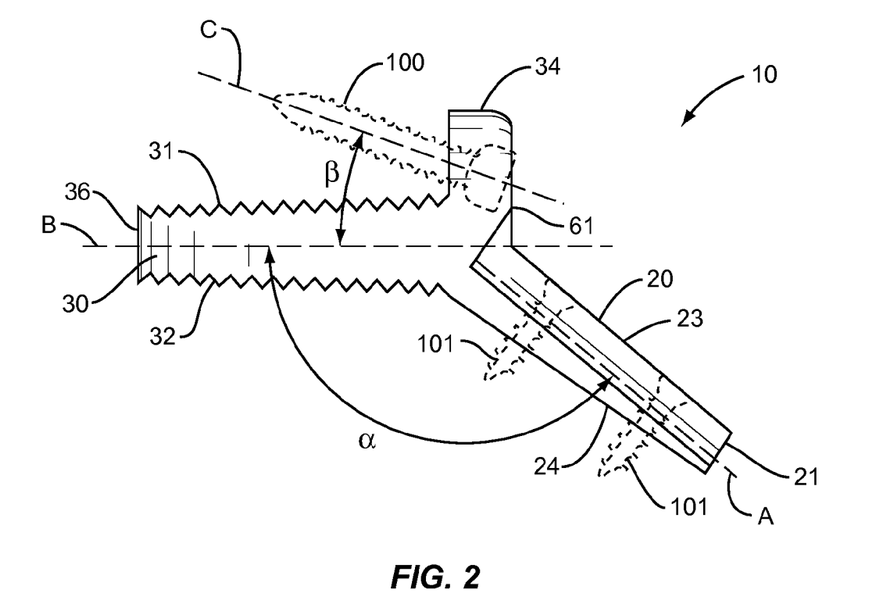
FIG. 2 is a side view of an implant according to one embodiment.
Figure 3:
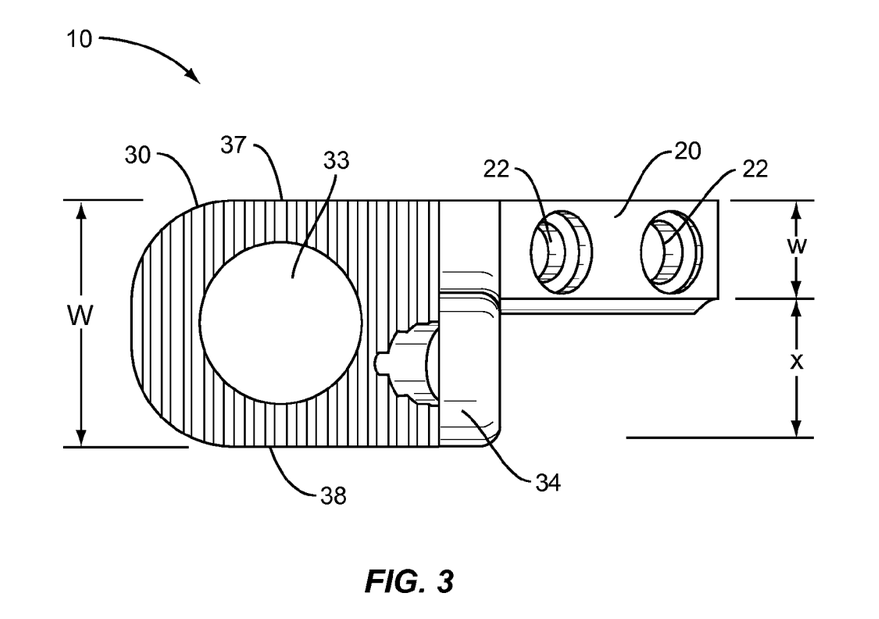
FIG. 3 is a top view of an implant according to one embodiment.

FIGS. 1-3 illustrate an implant 10 that generally includes a leg 20 and a blade 30. The leg 20 extends outward from the blade and includes an end 21 positioned away from the blade 30, and one or more apertures 22. The apertures 22 are each sized to receive a fastener 101 for attachment to the C2 vertebral member 120. The leg 20 may include a single aperture 22, or multiple apertures 22 depending upon the context of use. As best illustrated in FIG. 2, a thickness of the leg 20 measured between first and second sides 23, 24 may taper towards the end 21. The leg 20 includes a centerline A that extends along the length and through the end 21 and intersection with the blade 30 and between the first and second sides 23, 24. The leg 20 illustrated in FIGS. 1-3 is substantially straight.

The blade 30 includes a superior side 31 that contacts against the C1 vertebral member 110, and an inferior side 32 that contacts against the C2 vertebral member 120. One or both sides 31, 32 may be serrated or otherwise include a roughened surface to facilitate positioning between the C1 and C2 vertebral members 110, 120 and provide translational stability. Alternatively, one or both sides 31, 32 may be relatively smooth. A centerline B of the blade 30 extends through an insertion tip 36 and an opposing side 61, and between the superior and inferior sides 31, 32. The insertion tip 36 may include a bullet or tapered shape to facilitate insertion between the C1 and C2 vertebral members. An aperture 33 extends through the blade 30 and is used to contain bone graft, BMP, or other biological material.

A flange 34 extends outward above the superior side 31 of the blade 30 for placement along an exterior side of the C1 vertebral member 110. The flange 34 includes an aperture 35 sized to receive a fastener 100 and to position the fastener 100 for placement within the lateral mass of the C1 vertebral member 110. The aperture 35 includes a centerline C. Centerlines B and C form an angle $\beta$ that ranges from between about 20-40°. The centerline C may also be parallel with the centerline A of the leg 20. This relative positioning between the flange 34 and the leg 20 causes the fastener 100 that is positioned in the aperture 35 to be parallel to the leg 20. This would prevent the fastener 100 from angling too far upward in a superior direction and into a joint formed between the C0 and C1 vertebral members.

As best illustrated in FIG. 2, the flange 34 may extend substantially perpendicularly outward from the blade 30. FIG. 2 illustrates the flange 34 being substantially perpendicular to the centerline B of the blade 30. The flange 34 may also be positioned at a slight angle relative to the blade 30. The flange 34 may angle in a range of between about −10° to +10° relative to the centerline B of the blade 30.

The implant 10 is sized and shaped for the blade 30 to fit within the articular joint formed between the C1 and C2 vertebral members 110, 120, and for the leg 20 to attach to the C2 vertebral member 120. The leg 20 extends outward and downward in an inferior direction from the blade 30. FIG. 2 illustrates an angle $\alpha$ formed between the centerlines A and B. The angle $\alpha$ may range from between about 140°-170°. One specific embodiment includes the angle $\alpha$ being about 149°.

As best illustrated in FIG. 3, a width w of the leg 20 is smaller than a width W of the blade 30. Further, the leg 20 is offset along the width of the blade 30 with the leg 20 being in closer proximity to one of the sides 37 than to the other side 38. In the embodiment of FIG. 3, the side of the leg 20 is aligned with the side 37 of the blade 30. A straight line drawn through the center of each aperture 22 along the leg 20 is in closer proximity to the side 37 than to the side 38.

Further, the flange 34 includes a width x that is smaller than the width W of the blade 30. The flange 34 is laterally offset along the blade 30 and in closer proximity to the side 38 than to side 37. The flange 34 is also laterally offset from the leg 20. FIG. 3 includes the flange 34 completely offset from the leg 20. Other configurations may include just a partial offset. This offset positioning provides for insertion of the fasteners 100, 101 into their respective apertures 22, 35, and for the aperture 35 to align with the lateral mass of the C1 vertebral member and the apertures 22 to align with the C2 vertebral member. In one embodiment the width w of the leg 20 and the width x of the flange 34 are combined to be equal to the width W of the blade 30.

The implant 10 may include various dimensions to facilitate placement relative to the C1 and C2 vertebral members. In one embodiment, the leg 20 includes a length extending from the intersection with the blade 30 to the end 21 of about 17 mm. The blade 30 includes a length measured between the insertion tip 36 and the opposing side 61 of about 12 mm. This length fills the majority of the C1-C2 articular joint. The blade 30 includes a width W of about 8-10 mm to fill the articular joint from medial to lateral and centers the blade 30 in the articular joint and positions the flange 34 for the fastener 100 to start in the center of the C1 lateral mass. The blade 30 also includes a height measured between the superior and inferior sides 31, 32 of about 4-5 mm. This height is adequate for a strong blade 30 without causing excessive distraction between the C1 and C2 vertebral members.

Figure 4:
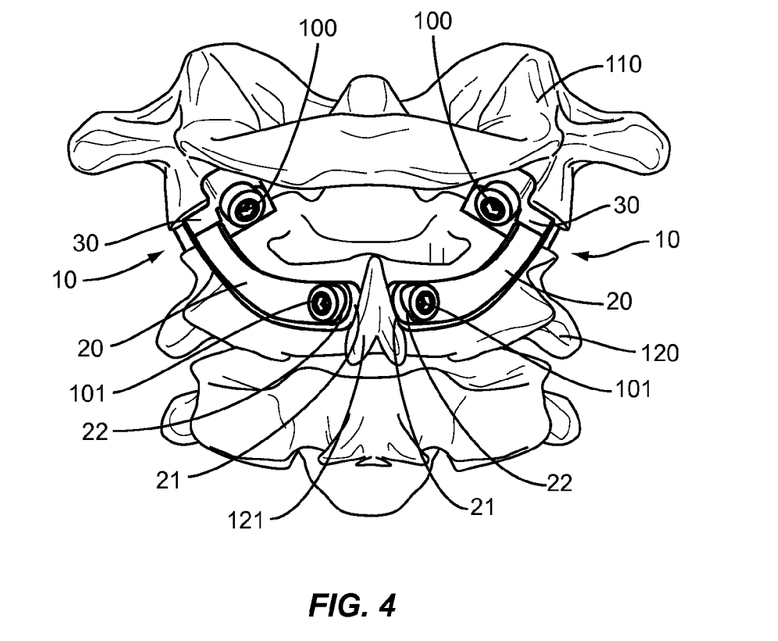
FIG. 4 is a posterior view of an implant attached to C1 and C2 vertebral members according to one embodiment.
Figure 5:
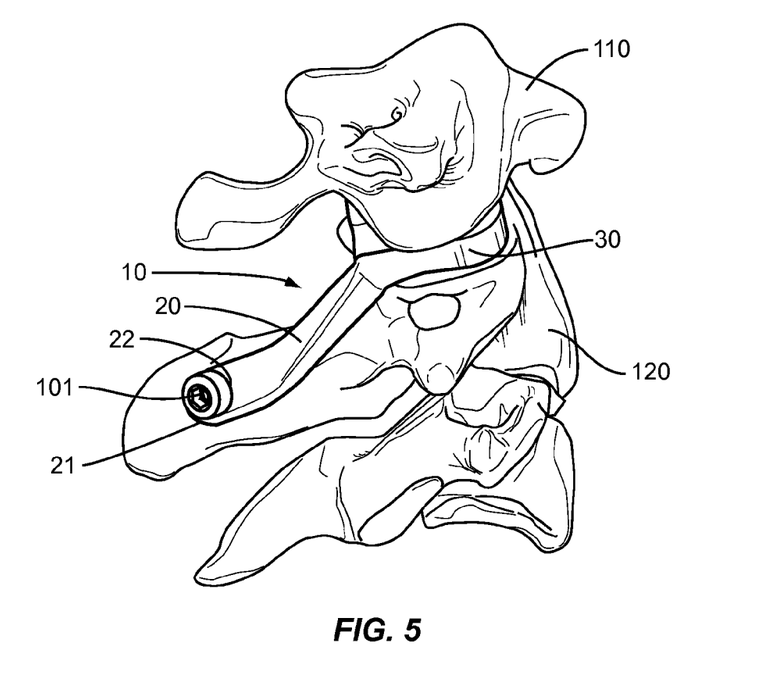
FIG. 5 is a sagittal view of an implant attached to C1 and C2 vertebral members according to one embodiment.

The leg 20 may include different shapes and sizes. FIGS. 4 and 5 include the leg 20 with a greater length between the intersection with the blade 30 and the end 21. The extended length places the end 21 in closer proximity to the spinous process 121 of the C2 vertebral member 120. The leg 20 is shaped to extend across the lateral mass and the lamina of the C2 vertebral member 120. As best illustrated in FIG. 5, the angle $\alpha$ formed between the blade 30 and the leg 20 provides for placement of the blade 30 in the articular joint and for the leg 20 to extend outward and inferiorly along the C2 vertebral member 120. The leg 20 may terminate short of the spinous process 121, or may extend along the spinous process 121. An aperture 22 in proximity to the end 21 is configured to receive a fastener 101. In one embodiment, the fastener 101 is a trans-laminar screw.

Figure 6:
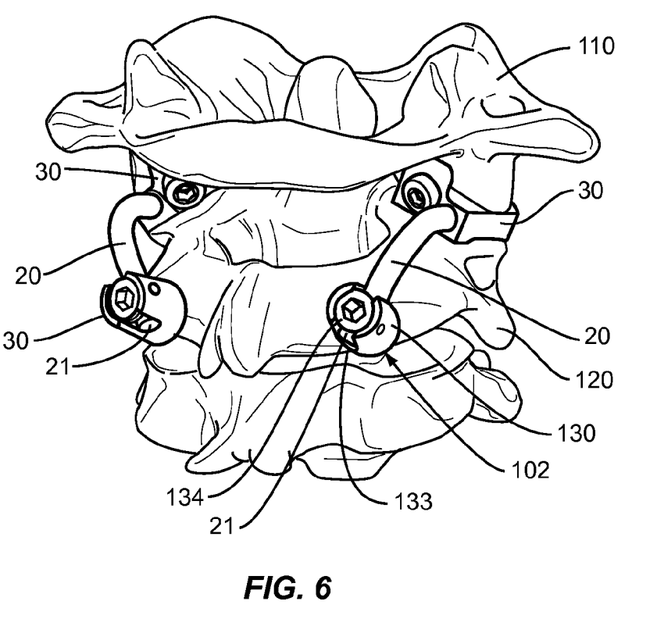
FIG. 6 is a perspective view of an implant attached to C1 and C2 vertebral members according to one embodiment.
Figure 7:
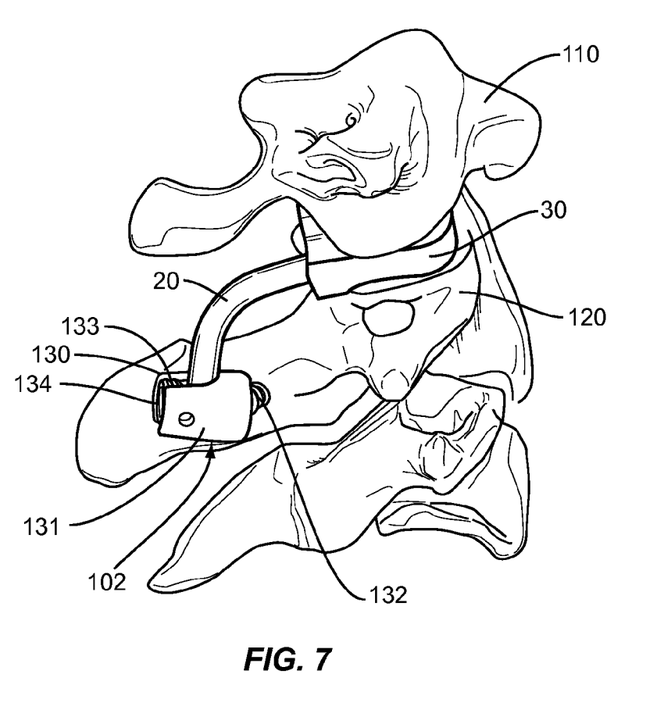
FIG. 7 is a sagittal view of an implant attached to C1 and C2 vertebral members according to one embodiment.

The leg 20 may also be configured to be attached to the C2 vertebral member 120 with a separate fastener 102 that receives the leg 20 as illustrated in FIGS. 6 and 7. The end 21 of the leg 20 includes a shape that fits into the fastener 102. The end 21 may include various cross-sectional shapes, such as circular, polygonal, oval, and star-shaped. As illustrated in FIGS. 6 and 7, the entire length of the leg 20 from the intersection with the blade 30 to the end 21 may include the same cross-sectional shape. Alternatively, the cross-sectional shape may vary along the length.

As illustrated in FIG. 7, the fastener 102 includes a receiver 131 and a shaft 132. The receiver 131 includes a channel 133 that receives the leg 20. A locking member 134 is configured to attach to the receiver 131 to maintain the leg 20 in the channel 133. The locking member 134 may include a set screw with exterior threads that mate with threads bordering the channel 133. Alternatively, the locking member 134 may include an annular shape with a threaded central opening that mate with threads on the exterior of the receiver 131. The shaft 132 extends outward from the receiver 131 and is threaded to engage with the C2 vertebral member 120. In one embodiment, the shaft 132 is fixedly connected to the receiver 131. In another embodiment, the shaft 132 is movably connected to the receiver 131 to adjust the angular position of the receiver 131. The movable embodiment may include the shaft 132 further including an enlarged head that fits within an interior reservoir of the receiver 131.

In another embodiment (not illustrated), the shaft 132 includes a hook that attaches to the C2 vertebral member 120. In one specific embodiment, the hook is sized to attach to an inferior side of the C2 lamina with the channel 133 positioned directly over the lamina of the C2 vertebral member 120.

The leg 20 extends outward from the blade 30 to be positioned within the fastener 102. As best illustrated in FIG. 7, the leg 20 may be shaped to be positioned away from the C2 vertebral member 120 between the blade 30 and the fastener 102. FIGS. 6 and 7 illustrate the end 21 placed within the fastener 102, although other placements may position the end 21 outward beyond the fastener 102.

Figure 8:
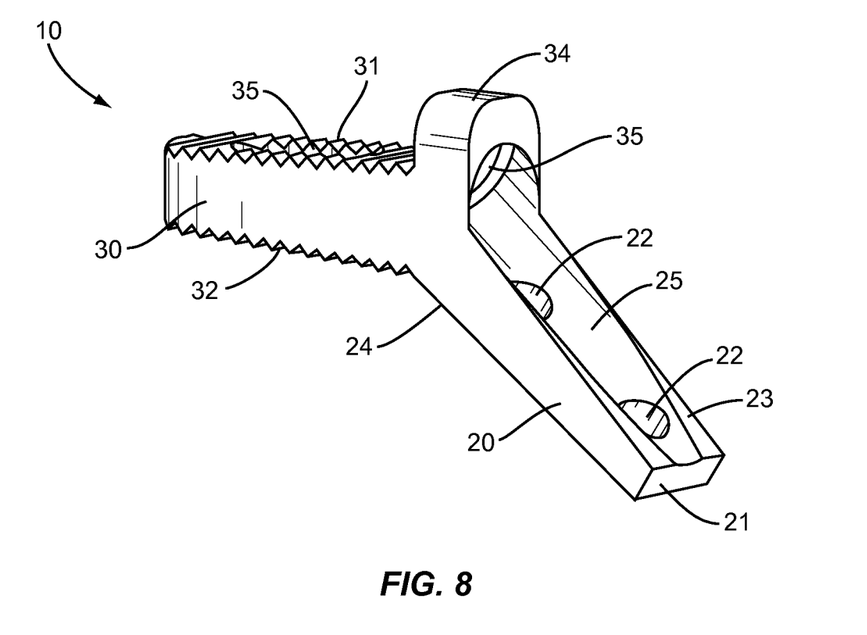
FIG. 8 is a perspective view of an implant according to one embodiment.
Figure 9:
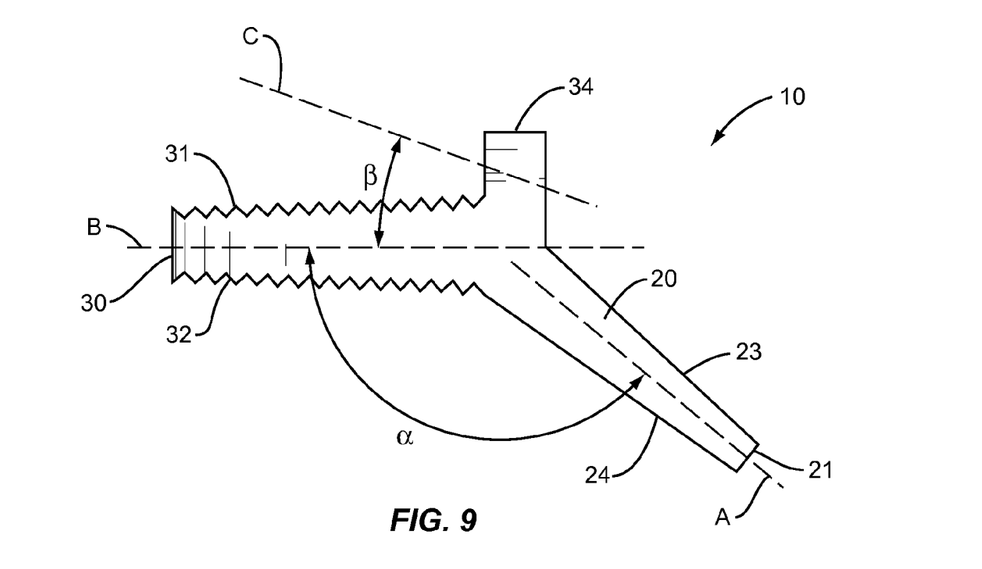
FIG. 9 is a side view of an implant according to one embodiment.
Figure 10:
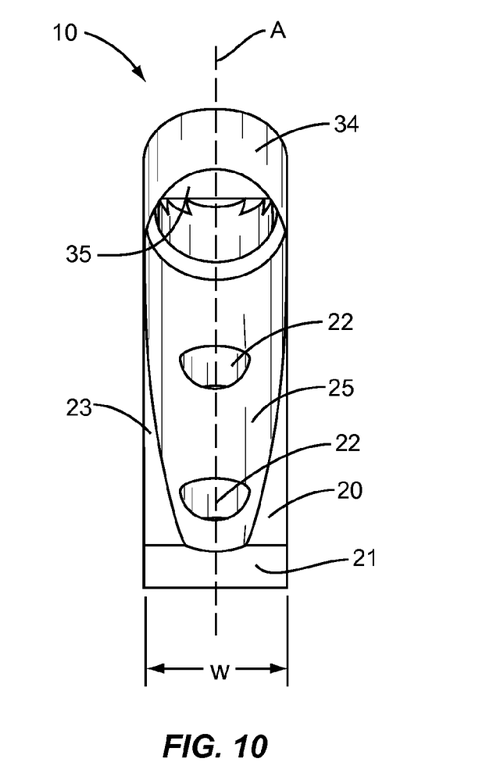
FIG. 10 is a rear view of an implant according to one embodiment.

FIGS. 8-10 include an implant 10 with the width w of the leg 20 being about the same as the blade 30. In one embodiment, the width of each of the leg 20 and the blade 30 is about 5 mm. The leg 20 is also aligned with the flange 34 with a straight line extending through a center of each of the apertures 22 extending through the aperture 35.

The first side 23 of the leg 20 is scalloped 25 and forms a curved indentation that accommodates a head of the fastener 100. As illustrated in FIGS. 8 and 10, the scallop 25 may increase in width from the end 21 towards the flange 34. Further, the scallop 25 may extend a length of the leg 20. FIGS. 8 and 10 include the scallop 25 extending from the intersection with the blade 30 to the end 21.

The aperture 35 in the flange 34 is sized for the fastener 100 to be positioned at an angle relative to the blade 30. The centerline C of the aperture 35 forms an angle $\beta$ with the centerline B of the blade 30. The angle $\beta$ is between about 20-40°.

In one embodiment, the aperture 35 of the flange 34 is wider thus allowing the fastener 100 to be positioned at a variety of angles. In one embodiment, the relative size between the aperture 35 and the fastener 100 can vary +/− about 20°.

The surgical procedure for implanting the implant 10 may vary depending upon the patient and the specific surgical criteria. In some surgical procedures, implants 10 would be implanted within each of the two C1-C2 articular joints. These procedures may include two identical implants 10, or the implants 10 may differ. Some surgical procedures may include implanting a single implant 10 within just one of the C1-C2 articular processes.

In one embodiment, the surgical procedure includes initially preparing the C1-C2 articular joint. Further, the articular joint and/or the C1 and C2 vertebral members 110, 120 are measured to determined the appropriately sized implant 10. Once the articular joint is prepared and the implant 10 is selected, the implant 10 is mounted in an implant holder and inserted into the patient. The insertion tip 36 is initially aligned with the joint and a force is applied to move the blade 30 into the joint. The implant holder may provide for impacting the implant 10 and moving the blade 30 into the articular joint. This process may use direct vision for placement relative to the C1 and C2 vertebral members 110, 120. The implant 10 restores the height lost between the C1-C2 articular joint which is common in arthritic patients.

The insertion of the blade 30 into the articular joint may position and orient the implant 10 and position the flange 34 relative to the C1 vertebral member 110 and the leg 20 relative to the C2 vertebral member 120. In one embodiment, positioning of the blade 30 between the C1-C2 vertebral members 110, 120 causes an angulation in the coronal plane by about 23° which tilts the leg 20 to the medial direction which is in the direction of the C2 lamina.

Figure 11:
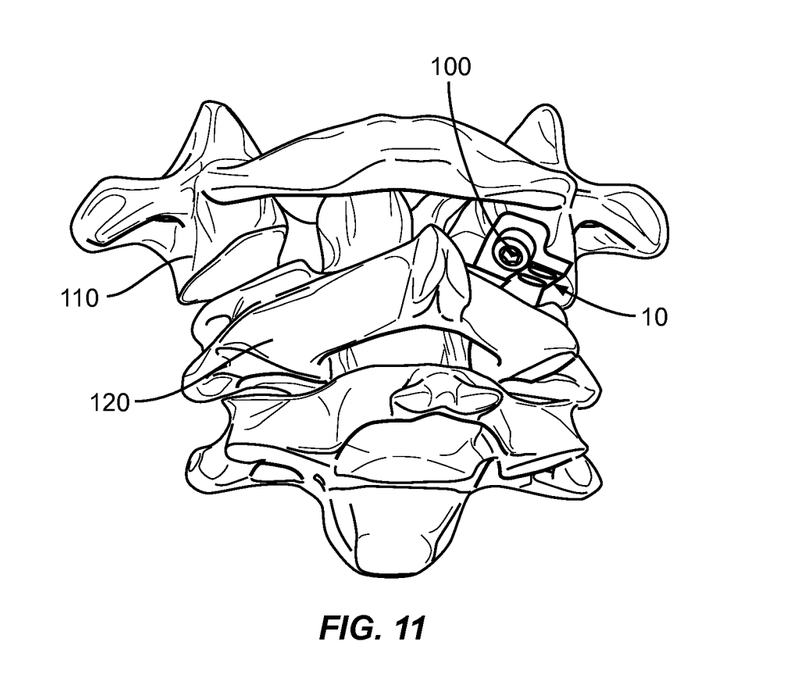
FIG. 11 is a posterior view of an implant being positioned within an articular joint between C1 and C2 vertebral members according to one embodiment.

FIG. 11 illustrates the implant 10 positioned relative to the C1 and C2 vertebral members 110, 120. Access to the C1 lateral mass is parallel to the C1 laminar. In some applications, the trajectory into the C1 lateral mass is about 40° to the horizontal. Once the implant 10 is aligned with the flange 34 aligned along an exterior of the C1 vertebral member 110, the C1 lateral mass is tapped and the fastener 100 is inserted. In one embodiment, the fastener 100 has a length of about 12 mm.

Figure 12:
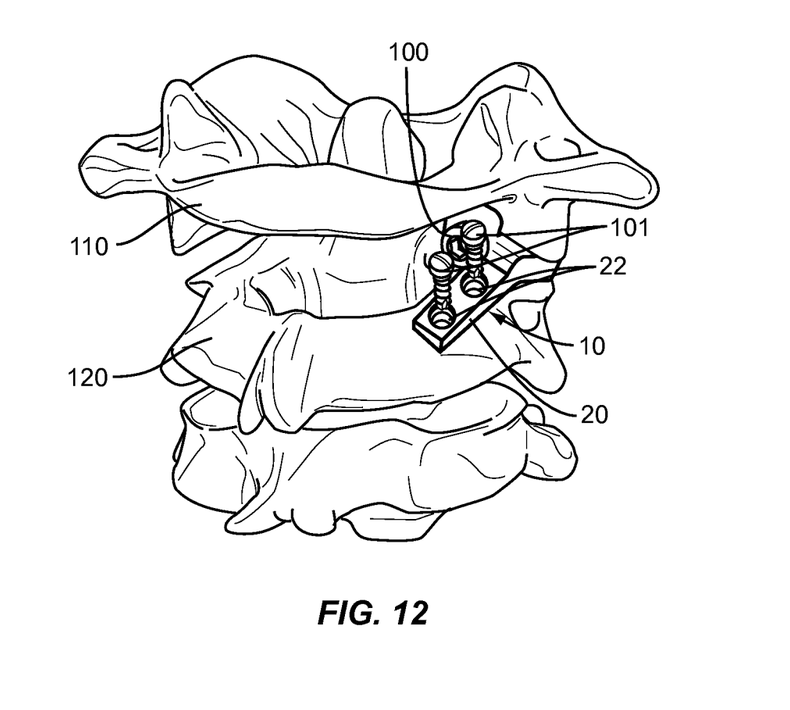
FIG. 12 is a posterior view of a pair of fasteners being inserted into a C2 vertebral member according to one embodiment.
Figure 13:
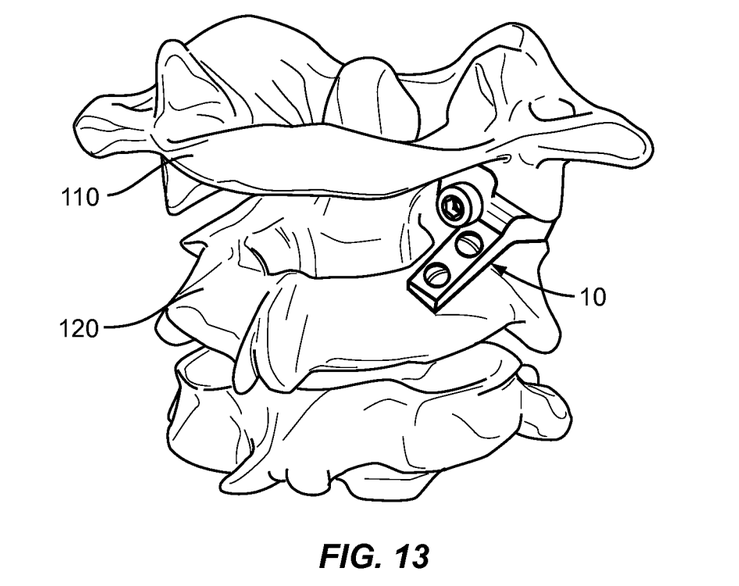
FIG. 13 is a posterior view of an implant positioned in a C1-C2 articular joint according to one embodiment.
Figure 14:
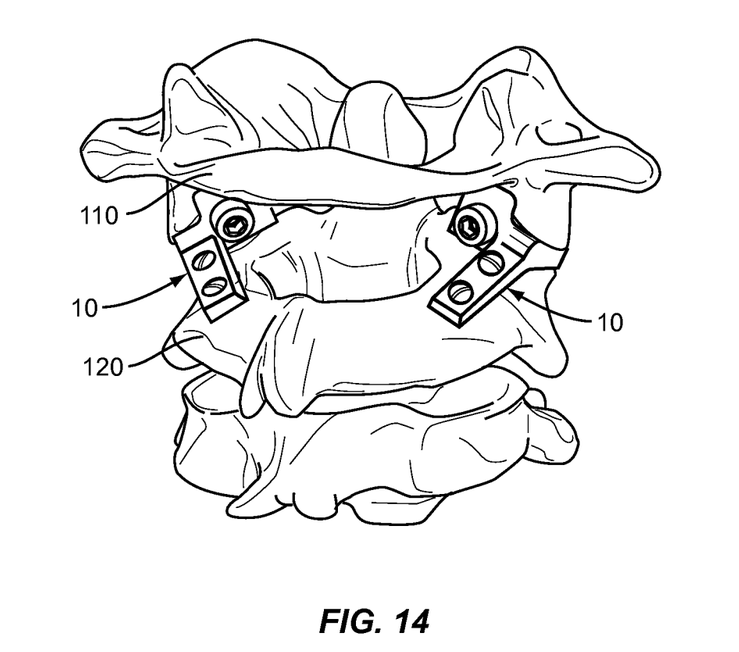
FIG. 14 is a posterior view of a pair of implants positioned in C1-C2 articular joints according to one embodiment.

As illustrated in FIG. 12, the leg 20 aligns along the laminar of the C2 vertebral member 120. The laminar is drilled and tapped and the fasteners 101 are inserted through the apertures 22. FIG. 13 illustrated the completed construct 10 attached to the C1 and C2 vertebral members 110, 120. In some embodiments, a single implant 10 is inserted into the patient. Other embodiments include a second construct 10 attached to the second articular joint as illustrated in FIG. 14.

Figure 15:
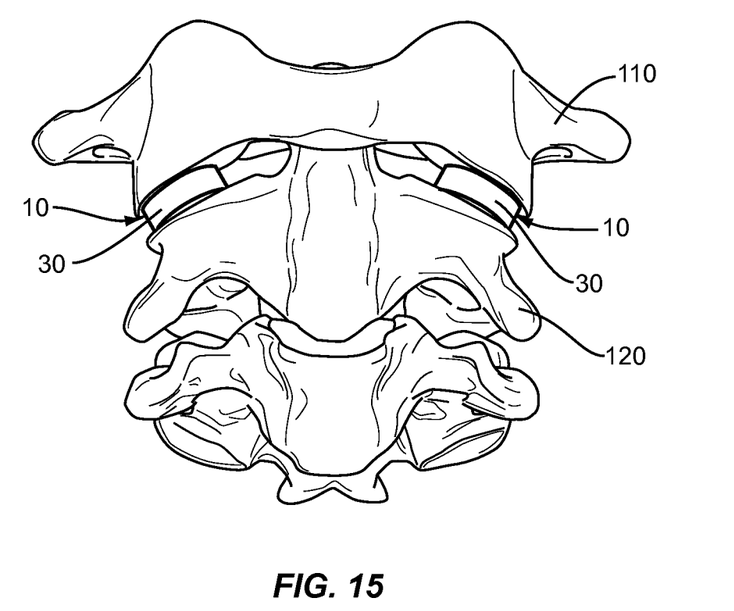
FIG. 15 is an anterior view of a pair of implants positioned in C1-C2 articular joints according to one embodiment.

FIG. 15 illustrates an anterior view of the placement of the pair of implants 10 relative to the C1 and C2 vertebral members 110, 120. The placement of the implants 10 positions the blades 30 within the articular joints.

Some implants 10 may not include a flange 34 and instead have the aperture 35 extend through the blade 30. This configuration positions aperture 35 for the fastener 100 to be placed in an orientation for a solid purchase into the C1 vertebral member 110.

Figure 16:
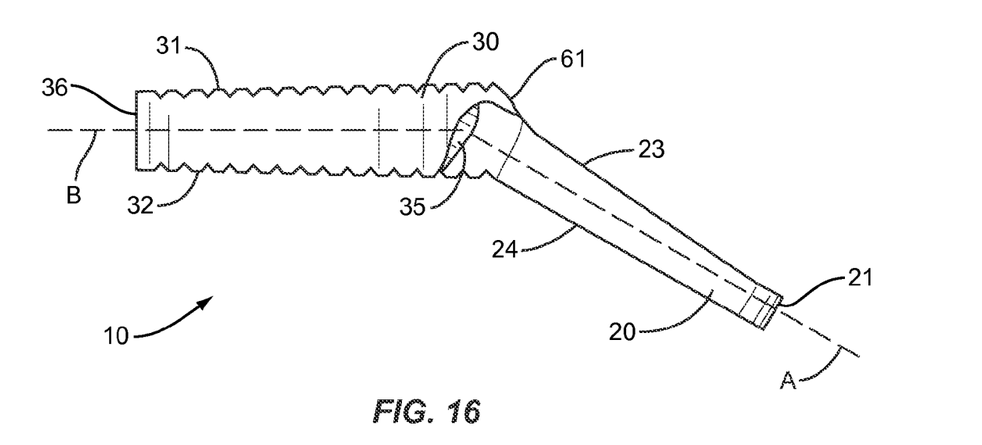
FIG. 16 is a side view of an implant according to one embodiment.
Figure 17:
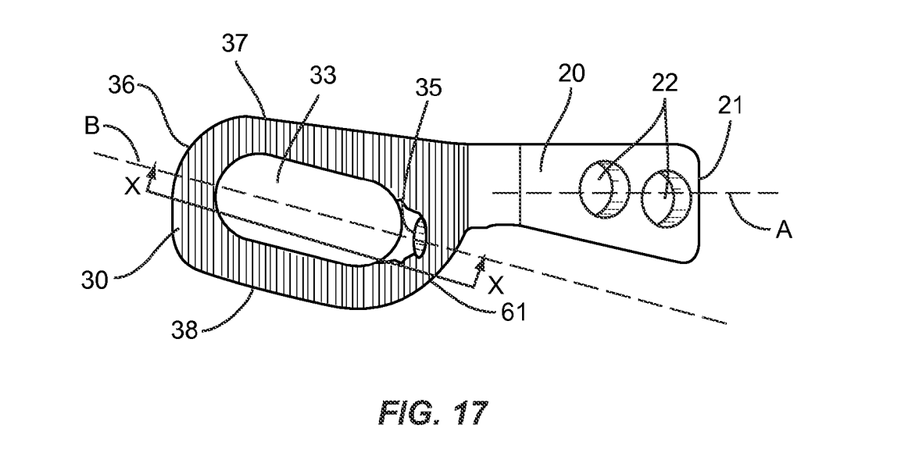
FIG. 17 is a top view of an implant according to one embodiment.
Figure 18:
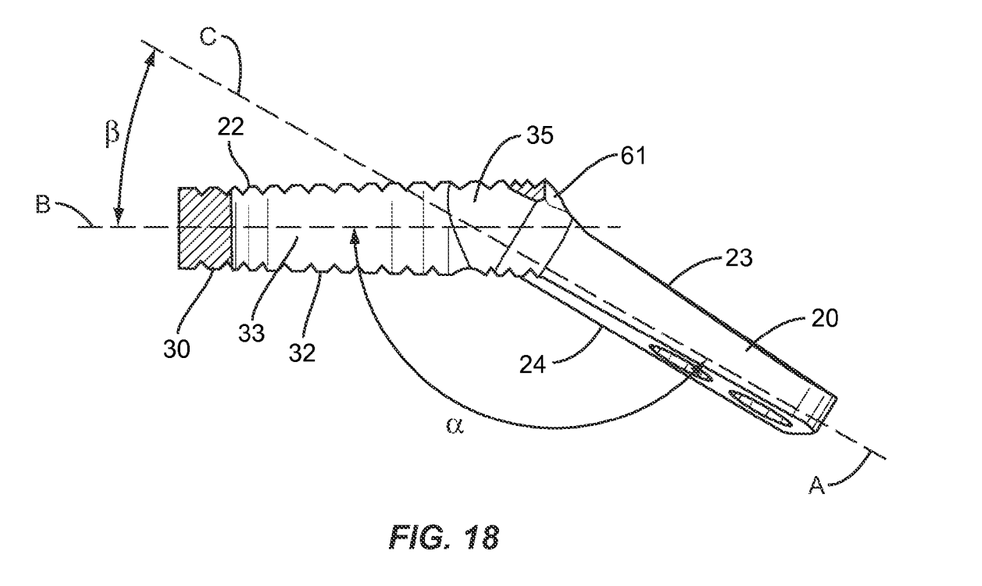
FIG. 18 is a sectional view of the implant of FIG. 17 cut along line X-X.

FIGS. 16-18 include an embodiment with the aperture 35 extending through the blade 30. The aperture 35 extends through a trailing or back section of the blade 30 and includes a centerline C that extends through a first end at the back side 61 and a second end at the aperture 33. In one embodiment, the aperture 35 is positioned between the superior and inferior sides 31, 32 of the blade 30. Other embodiments include the second end opening into the superior side 31.

As illustrated in FIG. 18, the aperture 35 is positioned at an angle $\beta$ relative to the centerline B of the blade 30. The first end of the aperture 35 at the side 61 is in closer proximity to the inferior side 32 than the second end of the aperture 35 at the aperture 33. As illustrated in FIG. 18, the angle $\beta$ formed by the centerline B of the blade 20 and the centerline C of the aperture 35 forms an angle $\beta$ in the range of between about 10°-45°. In one specific embodiment, the angle $\beta$ is about 30°.

FIG. 18 includes the centerline C of the aperture 35 being oriented at the same angle relative to the blade 30 as the centerline A of the leg 20. Other embodiments may include the centerlines A, C being at different angles. In one embodiment, the angle $\alpha$ is about 150°.

The blade 30 includes a height measured between the superior and inferior sides 31, 32 of about 3.2 mm. Further, the superior and inferior sides 31, 32 are at a slight angle relative to each other with the tip 36 being smaller than the opposing end at side 61. In one embodiment, the angle is about 3°.

As illustrated in FIG. 17, the leg 20 is positioned at a lateral angle relative to the blade 30. An angle formed between the centerline B of the blade 30 and a lateral side of the leg 20 is about 15°. Further, the leg 20 is laterally offset from the aperture 35 along the blade 30. This positioning facilitates access to the aperture 35 and prevents interference from the leg 20. As further illustrated in FIG. 17, the leg 20 may include a width that increases from the blade 20 towards the end 21. In one specific embodiment, the leg 20 includes a length of about 12.7 mm that extends from the intersection with the blade 30 to the end 21.

In another embodiment, the blade 30 does not include an aperture 33. The aperture 35 that receives the fastener for attachment to the C1 vertebral member 110 extends from a first end at the side 61 to a second end at the superior side 31.

The various aspects of the implants 10 described above may be interchangeable amongst the various embodiments. By way of example, the flangeless embodiment of FIGS. 16-18 may be used in combination with the leg 20 of FIGS. 6 and 7.

The implants 10 may be constructed from a variety of materials, including but not limited to polyetheretherketone (PEEK), hydroxyapatite (HA), and titanium.

The aperture 33 in the blade 30 may be completely contained as illustrated in FIG. 3. In another embodiment, the aperture 33 is not contained within the interior and is in communication with an exterior of the blade 30. In one specific embodiment, the blade 30 includes a substantially U-shape with the aperture 33 being enclosed on just three sides.

In some embodiments, one or more of the fasteners 101 may be replaced by a multi-axial pars screw. A screw would receive a rod that could extend in a first direction to the C0 vertebral member or in a second direction to the C3 vertebral member.

The implant 10 may be attached to the C1 and C2 vertebral members in various manners. In one embodiment, a fastener 100 attaches to the C1 vertebral member 110. The fastener 100 would have a width of about 4 mm. The fastener 100 may be bicortical with a range of lengths determined by a depth gauge determined under fluoroscopy. Lengths may include 14 mm, 18 mm, and 22 mm. In one embodiment, one or more fasteners 101 attach to the C2 vertebral member 120. The fasteners 101 include a length of about 7 mm.

The implants 10 may be implanted within a living patient for the treatment of various spinal disorders. The implant 10 may also be implanted in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is Claimed is:

1. An implant for positioning between C1 and C2 vertebral members comprising:
   a blade sized to fit between the C1 and C2 vertebral members and having a length measured between an insertion tip and a second side, a width measured between opposing first and second lateral sides and being perpendicular to the length, and a height measured between a superior side configured to contact against the C1 vertebral member and an inferior side configured to contact against the C2 vertebral member, the blade including a first aperture that extends through the blade between the inferior and superior sides, the blade including a blade centerline that extends through the insertion tip and the second side and between the inferior and superior sides;
   a flange at the second side of the blade that extends perpendicular to the blade centerline above the superior side of the blade to extend along an exterior face of the C1 vertebral member, the flange including a second aperture with a aperture centerline, the aperture centerline orientated at an angle of between about 20-40° relative to the blade centerline, the flange being perpendicular to the blade centerline and positioned away from the first aperture in a non-overlapping arrangement, a lateral side of the flange being aligned with the first lateral side and an opposite lateral side of the flange being positioned adjacent the blade centerline; and
   a leg at the second side of the blade that extends outward below the inferior side of the blade and away from second side of the blade to extend across an exterior of the C2 vertebral member, a lateral side of the leg being aligned with the second lateral side and an opposite lateral side of the leg being positioned adjacent the blade centerline
   wherein the leg includes a leg centerline that extends along a length of the leg, with an angle formed between the blade centerline and the leg centerline being between about 140°-170°.

2. The implant of claim 1, wherein the width of the blade is greater than the leg and the leg is laterally offset along the blade with the aperture centerline being laterally offset from the leg.

3. The implant of claim 1, wherein the leg includes at least two apertures with a line extending through a center of each of the apertures being in closer proximity to one of the lateral sides of the blade than the other lateral side.

4. An implant for positioning between C1 and C2 vertebral members comprising:
   a blade sized to fit between the C1 and C2 vertebral members and having a length measured between an insertion tip and an opposing second side and a blade width measured between opposing first and second lateral sides with the blade width being perpendicular to the length, the length of the blade defining an axis, wherein the blade includes a superior side configured to contact against the C1 vertebral member and an inferior side configured to contact against the C2 vertebral member, the blade including a blade aperture that extends through the blade between the inferior and superior sides;
   a flange at the second side of the blade that extends perpendicular to the axis above the superior side of the blade to extend along an exterior face of the C1 vertebral member, the flange including a flange width smaller than the blade width and including an aperture, the flange being offset along the blade width and in closer proximity to the first lateral side than to the second lateral side, a lateral side of the flange being aligned with the first lateral side and an opposite lateral side of the flange being positioned between the first and second lateral sides; and
   a leg at the second side of the blade that extends away from the second side of the blade and below the inferior side of the blade to extend across an exterior of the C2 vertebral member, the leg including a leg width smaller than the blade width and being offset along the blade width and in closer proximity to the second lateral side than to the first lateral side, a lateral side of the leg being aligned with the second lateral side and an opposite lateral side of the leg being positioned between the first and second lateral sides;
   wherein the blade includes a first centerline that extends through the insertion tip and the opposing second side and between the superior and inferior sides, and the leg includes a leg centerline that extends along a length of the leg, with an angle formed between the first centerline and the leg centerline being between about 140°-170°; and wherein the aperture in the flange includes a second centerline, with an angle formed by the first and second centerlines being between about 20-40°.

5. The implant of claim 4, wherein the leg is straight and includes first and second apertures with a line drawn through a center of the first and second apertures being straight and being spaced away from the flange.

* * * * *